United States Patent [19]
Koch

[11] Patent Number: 5,851,177
[45] Date of Patent: Dec. 22, 1998

[54] OTOSCOPE AND RHINOSCOPE DEVICE

[76] Inventor: Craig S. Koch, 6176 Reservoir Ct., Granite Bay, Calif. 95746

[21] Appl. No.: 63,854

[22] Filed: Apr. 21, 1998

[51] Int. Cl.$^6$ ..................................................... A61B 17/00
[52] U.S. Cl. ........................... 600/206; 600/233; 600/235
[58] Field of Search ..................................... 600/184, 201, 600/206, 208, 219, 226, 227, 233, 235

[56] References Cited

FOREIGN PATENT DOCUMENTS

| 1491478 | 7/1989 | U.S.S.R. ................................. 600/206 |
| 114051 | 3/1918 | United Kingdom .................... 600/233 |

*Primary Examiner*—Jeffrey A. Smith
*Attorney, Agent, or Firm*—Donald E. Nist

[57] ABSTRACT

The improved otoscope and rhinoscope device includes a resilient, flexible deformable ring with elastic memory. The ring is circular or oval and of metal, an elastomer such as plastic or rubber or of a plurality of interconnected springs of metal, plastic or the like. The ring has a groove on both the top and bottom thereof to receive on the top the forefinger of a medical practitioner and on the bottom the thumb of that practitioner. In the central cavity in the ring is secured a spaced pair of spreaders. Each spreader has a horizontal support bar extending transversely into the cavity, the two support bars being connected to opposite sides of the ring in the same plane and bearing on their free ends a spaced pair of spreader blades extending forwardly of the ring at about the midline thereof. The spreader blades have smoothly curved outer surfaces to engage the sidewalls of an ear canal or sidewalls of a nare when the ring is compressed vertically, thus increasing the spacing between the spreader blades. The spreaders can be of metal, plastic or the like. Since the ring is resilient, when compression is terminated the ring returns to its original shape. Three fingers and the entire palm of the hand holding the ring are available to stabilize a patient's head against movement. The spreader blades straighten the ear canal for proper viewing of it and the tympanic membrane without having to retract the pinna with the other hand.

8 Claims, 1 Drawing Sheet

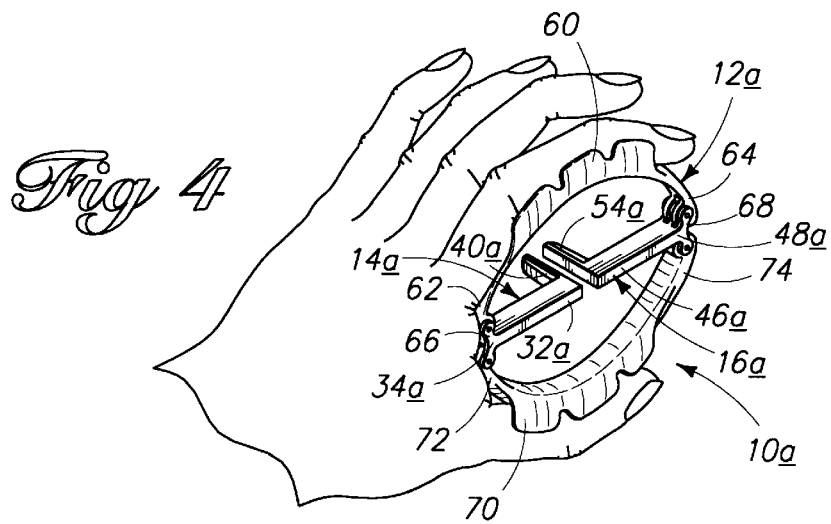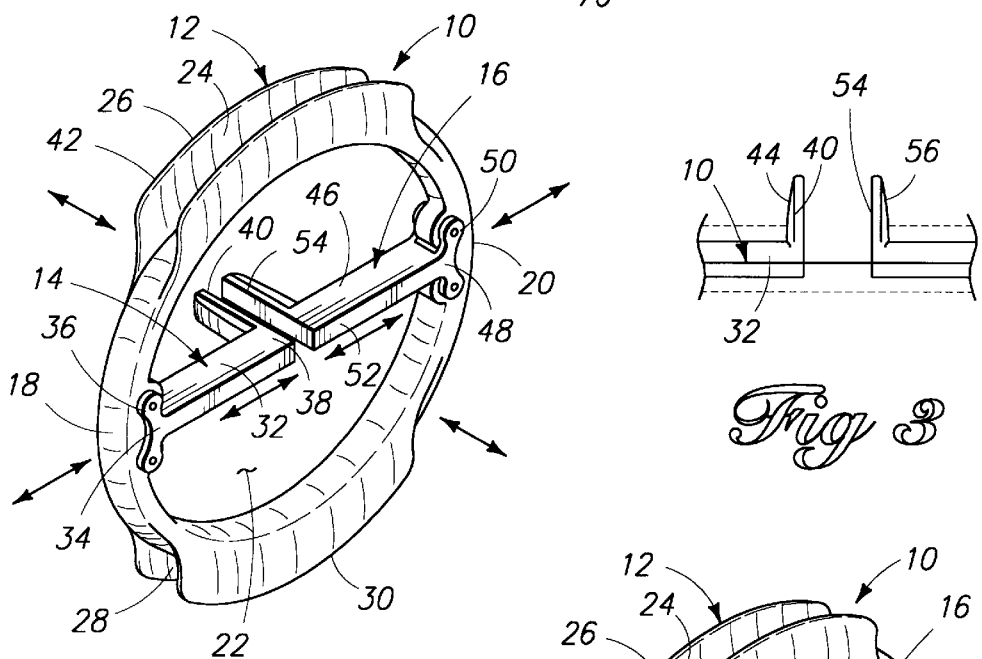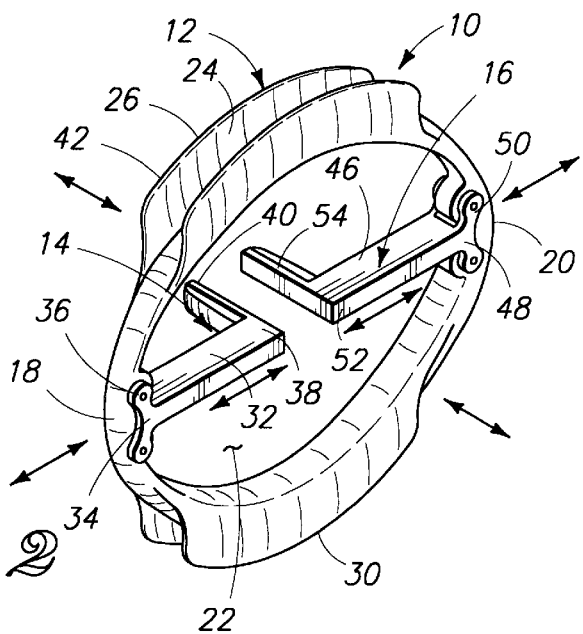

OTOSCOPE AND RHINOSCOPE DEVICE

BACKGROUND OF THE INVENTION

1. Field of the Invention

The present invention generally relates to medical devices and more particularly to an improved device which can be used efficiently as an otoscope and a rhinoscope.

2. Prior Art

Otoscopy is a procedure performed by medical practitioners in which the ear canal and tympanic membrane (eardrum) are examined in order to ascertain their physical condition and to remove cerumen (ear wax) and foreign objects from the ear canal, as well as to perform tympanocentesis (removal of fluid from the middle ear through the tympanic membrane).

Currently available otoscopes employ a speculum in the form of a cone with a narrow diameter front end, a wider diameter rear end and a central passageway for viewing the ear canal and tympanic membrane. The otoscope may also include a magnification lens and light source attached to the speculum or carried by the practitioner. Most otoscopes also have a long straight handle for holding the speculum.

The otoscopy procedure requires the the ear canal, which has a natural slight S-shaped curve, to be straightened in order to view the ear canal and tympanic membrane properly. In order the accomplish this, the speculum is placed in the outer portion of the ear canal, while the practitioner holds the otoscope handle in one hand with all fingers wrapped around therearound. The speculum is pressed against the ear canal wall to help straighten the ear canal, while the pinna is pulled backwards by the practitioner's other hand for the same purpose.

However, this procedure has certain drawbacks. Thus, only the back of the hand holding the otoscope is available to help the practitioner stabilize the patient's head against movement which would impede proper viewing of the ear canal and tympanic membrane. Moreover, any such head movement could cause the speculum to strike either of these structures, causing pain and possible injury thereto. Yet, the back of the hand is an inefficient means for such stabilization, having little surface area and feel.

Another problem with currently available otoscopes is that the front portion of the speculum is of narrow diameter, limiting the size of cerumen particles which can be withdrawn by an ear curette through the speculum pasageway. Moreover, the curette blocks the view of the cerumen when inserted though the speculum.

There is the additional problem of not having a free hand to manipulate the curette unless the pinna is released from the practitioner's hand, whereupon straightening of the ear canal is diminished. These problems are aggravated when the patient is a small child or infant requiring the use of reduced size equipment. Accordingly, there is a need for an improved otoscope which will obviate the foregoing problems.

Similar problems are encountered during use of currently available rhinoscopes which are used to survey nose nares (nostrils). Such rhinoscopes commonly use levers to spread the nares for easier viewing. However, these levers are usually elongated and thus spaced well apart from the patient's head so that head stabilization is difficult. Moreover, the levers are not useful in otoscopy.

Accordingly, there is a need for an improved instrument which can be used for both otoscopy and rhinoscopy, which instrument is simple, inexpensive, durable and efficient and which permits the practitioner to more readily view the affected parts of the patient while more efficiently stabilizing the patient against head movement and utilizing ancillary equipment such as curettes.

SUMMARY OF THE INVENTION

The improved otoscope and rhinoscope device of the present invention satisfies all the foregoing needs. The device is substantially as set forth in the Abstract of the Disclosure.

Thus, the device comprises, in combination, a flexible, resilient ring having elastic memory, and a bifurcated speculum connected to the ring, disposed within the central space of the ring and extending forwardly thereof. The ring can be fabricated of plastic or rubber, or can be formed of a pair of interconnected springs of metal, plastic or the like.

The bifurcated speculum comprises a spaced pair of aligned spreaders of any suitable material, such as metal, plastic or the like. Each spreader comprises a transversely extending support bar having a free end and an opposite end secured to one side of the ring, the two bars projecting into the central space of the ring from opposite sides of the ring. The spreaders each include a spreader blade connected to the free end of the support bar and projecting forwardly of the ring at about the midline thereof. The blades are parallel to each other but spaced apart, and the support bars are in the same plane, extending transversely of the ring.

When the ring is compressed vertically between the thumb and forefinger of the practitioner, the ring ovals and moves the spreader blades farther apart in order to perform the desired spreading of the ear canal walls and/or nares. The practitioner holds the ring in such a manner that the third, fourth and fifth fingers of the holding hand, as well as the palm of that hand, are available to more efficiently contact and restrain the head of the patient against movement. The fingers and palm are much more efficient than the back of the hand for such purposes. The extent of spreading of the blades is easily controlled by the practitioner's hand. When the procedure is completed, compression is terminated and the ring springs back to its original shape.

The ring preferably has a groove running along the top and bottom thereof to receive the thumb and forefinger for improved holding of the ring. The ring spreaders obviate the necessity of using the practitioner's other hand to pull the pinna backwards to straighten the ear canal. The spreader blades efficiently perform the desired straightening. Preferably, these blades are at about a 90 degree angle from the support bars and have smoothly curved outer surfaces to prevent ear canal irritation.

Since the practitioner's second hand is free, it can be used to help stabilize the patient's head or to manipulate an ear curette, nose curette or the like. When a curette is used, a clear view of the nare or ear canal and tympanic membrane is still retained due to the large opening between the spreader blades. Thus, the improved device of the present invention is equally suitable for use in otoscopy and rhinoscopy.

It will be understood that, if desired, one or more magnification lenses can be attached to the ring, and a light source can also be connected to the ring to enhance viewing by the practitioner.

Further features of the improved device of the present invention are set forth in the following detailed description and accompanying drawings.

DRAWINGS OF THE EMBODIMENTS OF THE INVENTION

FIG. 1 is a schematic rear perspective view, partly broken away, of a first preferred embodiment of the improved otoscope and rhinoscope device of the present invention, showing the ring thereof in an uncompressed state;

FIG. 2 is a schematic rear perspective view of the device of FIG. 1, showing the ring thereof in the vertically compressed state with the spreader blades thereof well separated for straightening an ear canal;

FIG. 3 is an enlarged schematic top plan view, partly broken away, of the spreader blades of the device of FIG. 1; and, FIG. 4 is a schematic rear perspective view of a second preferred embodiment of the improved device of the present invention, shown with the device being held between the thumb and forefinger of a medical practitioner and with the ring thereof in the uncompressed state.

DETAILED DESCRIPTION OF THE EMBODIMENTS

FIGS. 1–3:

Now referring to FIGS. 1–3 of the drawings, a first preferred embodiment of the improved otoscope and rhinoscope device of the present invention is schematically depicted therein.

Thus, device 10 is shown which comprises, in combination, a flexible, resilient ring 12 having elastic memory, and a spaced pair of spreaders 14 and 16 secured to ring 12, extending from opposite sides 18 and 20 thereof into central cavity 22 defined by ring 12 and estending forwardly thereof.

Ring 12 is fabricated of metal, elastomeric plastic or rubber and is circular or oval in outline in the relaxed uncompressed state shown in FIG. 1. A finger groove 24 runs along the top 26 of ring 12, while a similar thumb groove 28 runs along the bottom 30 of ring 12.

Spreader 14 can be fabricated of hard rubber, plastic, metal, ceramic or the like and comprises a horizontal elongated bar 32 extending transversely into cavity 22 at the transverse midline thereof, one end 34 thereof being secured by a bracket 36 to side 18 of ring 12 and the opposite free end 38 thereof having an integral forwardly extending spreader blade 40 at an angle of 90 degrees thereto. Blade 40 is of sufficient length to extend forward of the front end 42 of ring 12. Blade 40 has a smoothly curved outer surface 44 to engage without damaging a sidewall of an ear canal or nare sidewall.

Spreader 16 is similar to spreader 14. It comprises a horizontal bar 46 of identical length to bar 32 and in line therewith, bar 46 being connected at end 48 by a bracket 50 to side 20 of ring 12. The opposite free end 52 of bar 46 is integral with a forwardly extending spreader blade 52 similar to blade 40 and having a smooth curved outer surface 56. Blade 52 is spaced from blade 40 and aligned therewith at about the longitudinal centerline of cavity 22 and extends forward of ring 12, as shown in FIG. 1 to the same point as blade 40.

As shown in FIG. 2, when ring 12 is compressed vertically between the thumb and forefinger of a practitioner, if it is initially circular it becomes oval, with its greater diameter in a horizontal direction. If it is initially oval, it becomes more oval. In any event, the compression moves blades 40 and 54 farther apart (FIG. 2), thus spreading and straightening an ear canal or nare canal for better viewing of the interior thereof. When the compressing force is removed, ring 12 and blades 40 and 54 return to the uncompressed state shown in FIG. 1.

The degree of compression and thus the extent to which blades 40 and 54 are spread apart can be easily controlled by the practitioner. Sufficient spreading can be carried out to eliminate the need for the practitioner to retract the pinna rearwardly by the hand not holding the device. Thus, that hand is freed up to aid in stabilizing the patient's head and to operate a curette or other instrument in conjunction with device 10.

Thus, device 10 has improved capability over conventional otoscope and rhinoscopes.

FIG. 4:

A second preferred embodiment of the improved otoscope and rhinoscope device of the present invention is schematically depicted in FIG. 4. Thus, device 10a is shown. Components thereof similar to those of device 10 bear the same numerals but are succeeded by the letter "a". Device 10a is identical to device 10, except as follows:

a) Ring 12a comprises an elongated curved upper spring 60 of plastic or metal hinged at its opposite ends 62 and 64 to brackets 66 and 68, respectively, while ring 12a also includes an elongated curved lower spring 70 of the same length and dimensions as spring 60 and hinged at its opposite ends 72 and 74 to brackets 66 and 68.

b) Bars 32a and 46a are fixedly secured at ends 34a and 48a to brackets 66 and 68.

Ring 12a has the same over all shape and compressibility as ring 12 so as to spread blades 40a and 54a well apart during vertical compression of ring 12a for improved straightening of an ear canal and opening a nare canal. Ring 12a has the same shape-recovering characteristics as ring 12 when compression is removed. Accordingly, device 10a has substantially the advantages of device 10.

Various other modifications, changes, alterations and additions can be made in the improved otoscope and rhinoscope device of the present invention, its components and parameters. All such modifications, changes, alterations and additions as are within the scope of the appended claims form part of the present invention.

What is claimed is:

1. An improved otoscope and rhinoscope device, said device comprising, in combination:

a) a resilient, flexible deformable ring with elastic memory having a front end, a rear end and an annular sidewall, said ring being adapted to be held between the thumb and forefinger of a caregiver, said ring defining a central cavity extending from said rear end to said front end; and, b) a spaced pair of spreaders secured to opposite sides of said ring and disposed in said central cavity at about the longitudinal midline thereof, each said spreader comprising a transversely extending support bar having a free end and an opposite end secured to said sidewall, each said support bar bearing a spreader blade projecting forwardly from said free end to a position in front of said ring, said two spreader blades being spaced laterally from each other at about said midline, whereby compressing said ring vertically between said thumb and forefinger ovals said ring and increases the spacing between said spreader blades for widening the field of view through an ear canal or nostril of a patient into which said spreader blades are inserted and whereby terminating said compression moves said spreader blades toward each other for easy withdrawal from an ear canal or nostril and returns said ring to its original shape for reuse.

2. The improved device of claim 1 wherein said spreader blades have curved outer surfaces to non-frictionally engage the walls of an ear canal or nostril, and whereby said spreader blades are at about a 90 degree angle from said support bars.

3. The improved device of claim 2 wherein said ring has an annular recess along the top thereof into which the forefinger of the caregiver can be placed and wherein said ring has a similar annular recess along the bottom thereof into which the thumb of the caregiver can be placed when using said device.

4. The improved device of claim 1 wherein said ring in the uncompressed state is about circular in outline.

5. The improved device of claim 1 wherein said ring in the uncompressed state is oval with a greater horizontal diameter than vertical diameter and wherein said ring in the compressed state has an increased horizontal diameter over that of the uncompressed state.

6. The improved device of claim 5 wherein said support bars extend along the horizontal midline of said ring.

7. The improved device of claim 1 wherein said ring comprises one of resilient plastic and rubber.

8. The improved device of claim 1 wherein said ring comprises a pair of springs, one end of each said spring being connected to a first connector at one side of said ring and wherein the opposite end of each said spring being connected to a second connector at the opposite side of said ring.

* * * * *